United States Patent [19]

Familletti

[11] Patent Number: 5,073,491
[45] Date of Patent: Dec. 17, 1991

[54] IMMOBILIZATION OF CELLS IN ALGINATE BEADS CONTAINING CAVITIES FOR GROWTH OF CELLS IN AIRLIFT BIOREACTORS

[75] Inventor: Philip C. Familletti, Millington, N.J.

[73] Assignee: Hoffman-La Roche Inc., Nutley, N.J.

[21] Appl. No.: 289,647

[22] Filed: Dec. 23, 1988

[51] Int. Cl.$^5$ ........................ C12N 5/00; C12N 11/10; C12N 5/02; C12M 1/40
[52] U.S. Cl. ............................... 435/240.22; 435/178; 435/182; 435/240.25; 435/252.1; 435/254; 435/288; 435/313
[58] Field of Search ........... 435/240.2, 240.22, 240.24, 435/240.25, 174, 177, 178, 182, 288, 313, 252.1, 254

[56] References Cited

U.S. PATENT DOCUMENTS

| 4,572,897 | 2/1986 | Amatz et al. | 435/177 |
|---|---|---|---|
| 4,649,117 | 3/1987 | Familleffi | 435/240.24 |
| 4,798,786 | 1/1989 | Tice et al. | 435/182 X |
| 4,935,365 | 6/1990 | Nilssan et al. | 435/178 |

OTHER PUBLICATIONS

"Air lift Fermenters: Construction Behavior and Uses". Advances in Biotechnology Processes I, pp. 67–95 1983, Alan Liss, New York, NY.
"Techniques for Mammalian Immobilization", Bio/-Technology, vol. 6 pp. 41–44, Jan. 1988.
"Fermentation Special Report", Bio/Technology, vol. 6 pp. 506–516 (May, 1988).
"Preparation of Immobilized Animal Cells" FEBS Letters, vol. 118, No. 1, pp. 145–150, Aug. 1980.
"Immobilized Plant Cells for the Production and Transformation of Natural Products", FEBS Letters, V. 103, No. 1, Jul. 1979.
"Entrapment of Plant Cells in Different Matrices", FEBS Letters V. 122, No. 2, pp. 312–316, Dec. 1980.
Arathoon, W. R., et al, Science 232:1390 (1986).
Knorr, D. et al, Food Technol. 39:135 (1985).
Chibata, I. Ann. Rev. Biophys. Bioeng. 10:197 (1981).
Shirai, Y. et al., Appl. Microbiol. Biotechnol. 26:4951–499 (1987).
Staehlin, T. et al PNAS 78:3 pp. 1848–1852 (1981).
Inhomogenous Polysaccharide Ionic Gels, Carbonhydrate Polymers, v. 10, pp. 1–24 (1989).

*Primary Examiner*—David M. Naff
*Attorney, Agent, or Firm*—George M. Gould; Bernard S. Leon; George W. Johnston

[57] ABSTRACT

Method and apparatus are provided for immobilizing and growing cells in airlift bioreactors to obtain increased cell density. Cells are immobilized by forming alginate beads containing cells and gelatin particles, and dissolving the gelatin by heating to form cavities in the beads entrapping the cells. In a growth chamber of an airlift bioreactor, introduced oxygen-containing gas circulates growth medium in contact with the beads resulting in oxygen transfer to cells in the cavities of the beads where growth of the cells occurs. Preferably, bead formation is carried out in the growth chamber by dripping an alginate-cell gelatin suspension into a calcium solution contained in the growth chamber. Growth medium is then supplied to the chamber, and oxygen-containing gas is introduced to result in circulation of the growth medium and growth of the cells.

7 Claims, 2 Drawing Sheets

IMMOBILIZATION OF CELLS IN ALGINATE BEADS CONTAINING CAVITIES FOR GROWTH OF CELLS IN AIRLIFT BIOREACTORS

FIELD OF THE INVENTION

This invention relates to airlift bioreactors having a semi-solid support material made of a polymer matrix incorporating a gelatin material to facilitate immobilization and growth of cells, as well as methods of operating the same.

BACKGROUND OF THE INVENTION

Natural and recombinant products are in growing demand for research and therapy. Large scale production of such cell products has traditionally tended to the use of larger vessels for more production. See, for example, Arathoon, W. R., et al., *Science* 232:1390 (1986). Whereas large vessels may be satisfactory for bacterial fermentations, such vessels do not provide adequate circulation or nutrients, etc. necessary for the growth of eucaryotic cells, such as mammalian or plant cells.

To increase product yields, various immobilization procedures used in bioreactors have been developed. Immobilization procedures increase the cell density of the culture, which results in increased productivity and, therefore, smaller volume bioreactors may be used. Various immobilization procedures include the carrier-binding method, the cross-linking method and the entrapping method. The carrier-binding method is based on direct binding of cells to water-insoluble carriers by physical adsorption, ionic and/or covalent bonds. Cells may also be immobilized by cross-linking each other with bi- or multi-functional reagents. Finally, a method of entrapping cells into polymer matrices has been developed.

The various types of immobilization procedures may be used in bioreactors such as airlift bioreactors known in the art. See, for example, "Airlift Fermentors: Construction Behavior and Uses", *Advances in Biotechnology Processes I*, pp 67-95, Alan R. Liss, New York, N.Y. (1983).

A particular commercially available airlift bioreactor which can be readily modified according to the present invention has an upper growth chamber which is connected to a lower smaller diameter mixing chamber via a downwardly and inwardly sloping conical section. A gas mixture is sparged into the mixing chamber and sets up a gentle circulation of liquid growth medium within the growth chamber. This bioreactor accomodates immobilization procedures for both suspension cells and for attachment dependent cells.

Anchorage dependent cells are those cells which must be grown in an environment wherein they can be attached to a support material. This attachment has been accomplished, for example, by attaching cells to stacked petrie dishes or by growing the cells in roller bottles. Each of these approaches has drawbacks such as the inability to achieve high volumetric cell density or inadequate circulation of nutrients, etc. necessary to grow the cells.

Certain cell lines are suspension cells as is well known in the art. This means that the cells must be grown in an environment where they are suspended in a liquid growth medium and circulated to provide adequate contact with nutrients and dissolved gases to promote cell growth. Suspension cells, such as hybridomas, may be immobilized by entrapment in polymer matrices in the form of beads which are then circulated within the liquid growth medium in the bioreactor.

SUMMARY OF THE INVENTION

According to the invention, airlift bioreactors are improved by including a cell immobilization material in their growth chambers for increasing cell density and increasing gas absorption from a liquid growth medium circulating within the growth chamber into the immobilization material.

More particularly, the cell immobilization material is a polymer matrix composed of a polymer material, protein particles and immobilized cells. The polymer matrix is formed by polymerizing the polymer material and entrapping the gelatin particles and cells. The matrix is then incubated at an elevated temperature which will dissolve the entrapped gelatin particles to form cavities within the matrix. The matrix is positioned in a growth chamber of a bioreactor, and the cells grow within the formed cavities increasing cell density and thus improving large scale production of the cells. Preferably the polymer matrix is formed from an alginate material and the protein particles are preferably gelatin.

Additionally, the invention provides a method of growing cells in airlift bioreactors having growth chambers which include the immobilization material and a method for manufacturing the immobilization material.

DETAILED DESCRIPTION OF THE INVENTION

Figure 1:
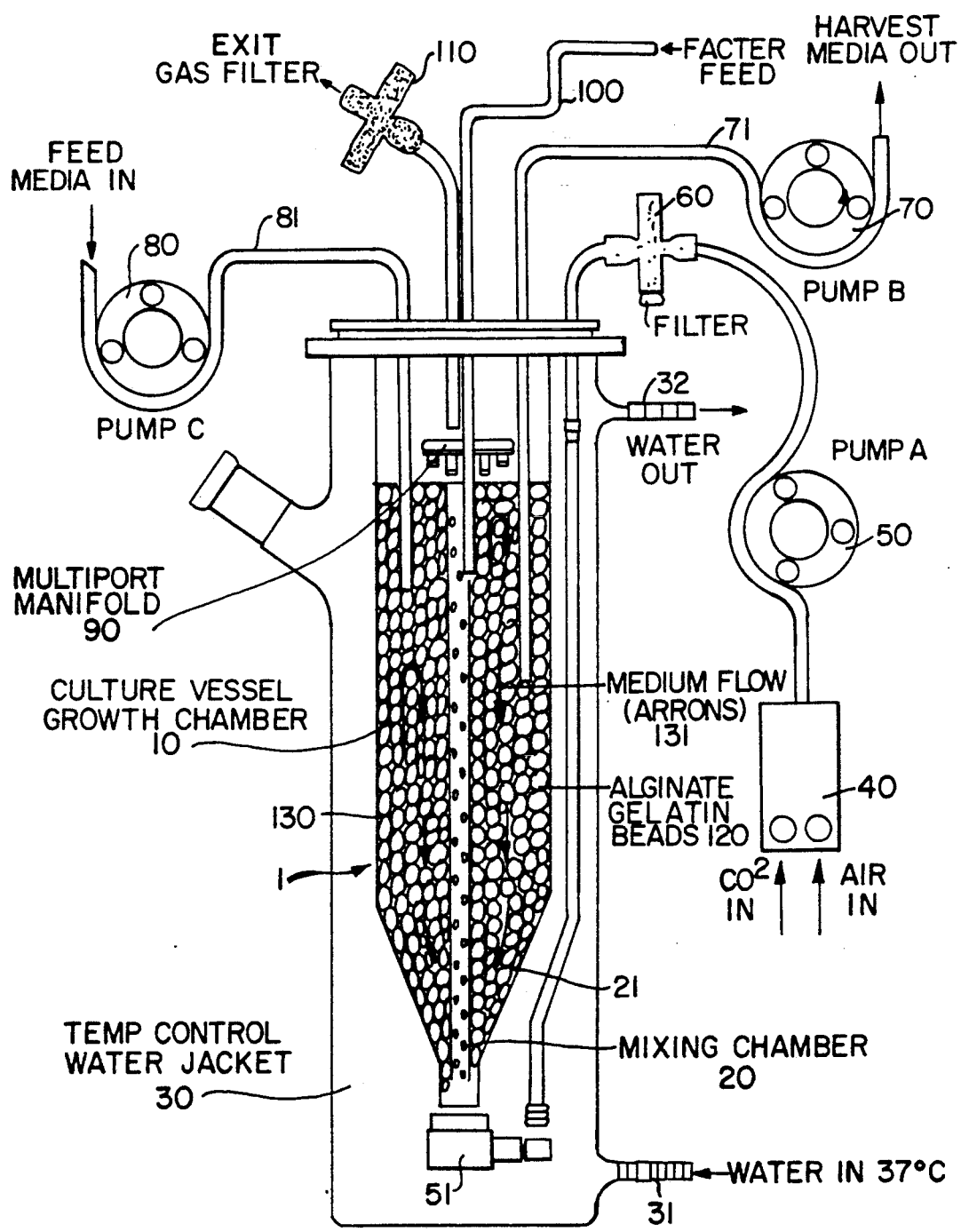
FIG. 1—is a schematic cross section of an airlift bioreactor having alginate/gelatin beads as a semi-solid support material in its growth chamber according to a preferred embodiment of the invention.

As used herein, the term "suspension cells" shall refer to any cells, particularly mammalian cells, which will grow and multiply when suspended in a liquid growth medium. Examples of suspension cells which may be grown using the apparatus and method according to the invention include, but are not limited to, hybridoma cells that produce monoclonal antibodies to human alpha-interferon and monoclonal antibodies to human IL1.

The term "anchorage cells" shall refer to any cells particularly mammalian cells, which will grow and multiply when attached to a support material and shall include but are not limited to cells which will only grow when attached to a solid support material. Examples of anchorage cells which may be grown using the apparatus and methods according to the invention include but are not limited to Chinese Hamster Ovary cells, ATTC No. CCL-61.

The term "liquid growth medium" shall refer to any liquid medium in which cells may be grown. A particularly preferred growth medium for use in growing mammalian cells according to the present invention is Iscove's Modified Dulbecco's Medium supplemented with heat inactivated fetal calf serum.

The term "cell immobilization material" shall refer to any material which is placed within the airlift bioreactor which traps gas bubbles from the circulating liquid growth medium and which immobilizes cells without totally disrupting gentle circulation of the liquid growth medium within the bioreactor. Preferably, the cell immobilization material is a polymer matrix containing a polymer material and gelatin particles which is formulated into beads to import a high volumetric area. More preferably, the cell immobilization material is formed from an alginate and gelatin particles.

The term "polymer matrix" shall refer to a polymerized matrix composed of any polymer material known in the art which is liquid in a nonpolymerized state and which is semi-solid in a polymerized state and which does not disrupt the growth of cells entrapped within the polymer matrices, and particles which solidify at about room temperature and which liquify at elevated temperatures without disrupting the growth of the entrapped cells and which form cavities within the polymerized matrix in which the entrapped cells grow. Preferably the matrix is polymerized in the shape of beads. Polymer materials which polymerize to form polymer matrices, include but are not limited to, alginate, carageenin, chitin, and agarose. Especially preferred is the use of alginate as the polymer matrix.

The term "alginate" shall refer to any of the conventional salts of algin, a polysaccharide of marine algae which may be polymerized to form a matrix for use within the growth chamber of the bioreactor. The salts of algin shall include, but are not limited to, any metal salt such as sodium, magnesium, etc. Preferably, the alginate includes, but is not limited to, a composition of gluronic and mannuronic acids and the material has a low viscosity.

The term "gelatin" or "gelatin particles" refers to any albumin obtained by boiling animal tissue under pressure with water. Preferably, the gelatin is obtained from mammalian tissue, and more preferably is obtained from either porcine or bovine skin.

The term "carageenin" refers to a galacton obtained by extraction of various red seaweeds known in the art. The structure of carageenin is a mixture of polysaccharides which varies with the seaweed source.

The term "agarose" refers to a neutral gelling fraction of a polysaccharide complex extracted from the agarocytes of algae such a Rhodophyceae.

The term "elevated temperatures" refers to any temperature above room temperature which liquifies the gelatin particles.

As noted above the preferred cell immobilization material of the present invention is a polymer matrix composed of a polymerizing material, entrapped cells, and particles which liquify at elevated temperatures to form cavities in the polymer matrix in which the immobilized cells grow.

The preferred polymer material is alginate which polymerizes from a liquid solution when exposed to polyvalent cation ions to form the immobilization material. Cells to be immobilized and grown are preferably mixed with a solution containing gelatin particles and the cell-gelatin solution is in turn mixed with the alginate solution, polymerized and incubated to form cavities within the polymer matrices as described infra.

Conventional alginate beads used as polymer matrices are obtained by converting water soluble sodium alginate to insoluble calcium alginate in accordance with procedures well known in the art. See for example, Knorr, D. et al., *Food Technol.* 39:135 (1985); Chibata, I., *Ann. Rev. Biophys. Bioeng.* 10:197 (1981) and Shirai, Y. et al., *Journal Appl. Microbiol. Biotechnol.*, 26:495 (1987); herein incorporated by reference.

To prepare the cell immobilization material of the present invention, a cell line is grown by conventional procedures in spinner flasks as described in *Methods in Enzymology.* ed. by W. B. Jakoby, et al., vol. 58 (Acad. Press 1979) herein incorporated by reference.

The cultured cells are concentrated, resuspended in a conventional sterile gelatin suspension and then mixed with a sodium alginate solution.

A solution of $CaCl_2$ and NaCl is placed in a growth chamber, such as in a flask or in a bioreactor. The resulting alginate-gelatin-cell suspension is then pumped through a multiport manifold and dripped into the calcium solution in the growth chamber at about room temperature. On contact with the calcium solution, the alginate polymerizes as is known in the art, to form beads. See Knorr, supra. Within the beads are trapped the gelatin particles and the cultured cells. The beads are then washed with a growth medium to remove excess calcium and incubated at about 37° C. As the temperature increases from room temperature to 37° C., the gelatin particles liquify and form cavities within the alginate beads.

Gelatin particles derived from mammalian tissue and produced by the Sigma Company are used to prepare the sterile gelatin suspension of the invention. Any mammalian source may be used which produces a gelatin which liquifies at elevated temperatures, which solidifies at room temperature (i.e. about 23° C.), and which does not affect the growth of the cells being cultured in the bioreactor. Preferred gelatin sources are bovine or porcine skin gelatin particles having a 300 bloom number. Bloom number is an indication of the strength of the gels produced and the higher the bloom number the stronger the gel. Especially preferred are porcine skin gelatin particles.

The gelatin particles form cavities in the alginate by liquifying within the polymer matrices at elevated temperatures and the cells entrapped within the matrices grow in these cavities uninhibited by the density of the gel while still being trapped by the alginate. Additionally, the gelatin cavities serves to reduce the rigidity of the matrices to flex the alginate beads to thus increase diffusion of gases and nutrients from the liquid growth medium into the beads.

It is noted that any type of particles, besides the gelatin particles, which liquify at elevated temperatures, solidify at room temperature and form cavities within the polymer matrix without affecting the growth of the entrapped cells, may be used in the present invention to from the immobilization material. Such particles include, but are not limited to, parafin wax.

To form the gelatin particles suspension, sterile gelatin is added to liquid growth medium and the suspension is kept at room temperature to ensure that the gelatin does not dissolve. The gelatin suspension preferably contains about 2.5% to about 25% weight/volume gelatin particles. Especially preferred is a 2.5% weight/volume gelatin particles suspension.

An alginate solution is prepared by mixing sodium alginate in a growth medium and a NaCl solution. A preferred alginate solution contains about 0.85% to about 4% weight/volume alginate, and an especially preferred solution contains about 0.85% weight/volume alginate.

The alginate solution containing the resuspended hybridoma cells and gelatin particles is pumped through a tube, preferably a 5 mm tube, and dripped into a growth chamber of the bioreactor containing a calcium solution to form beads which are preferably 8 mm in diameter. Preferably the calcium solution contains 50 mM $CaCl_2$ and about 0.1M NaCl. The gelatin-cell containing alginate beads are washed three times in growth medium in the bioreactor and incubated at about 37° C. to dissolve the gelatin within the alginate beads to form cavities in which the cells may grow.

The bioreactor maintains the immobilized cell cultures at an optimum PH, preferably in the range of about pH 6.7-7.3 by increasing the rate of perfusion of growth medium as needed.

Cells entrapped in the immobilization material positioned in the bioreactor according to the present invention have been observed to increase in density as much as three-fold in comparison to cells immobilized in conventional alginate.

Cells entrapped in conventional alginate beads known in the art which are formed without incorporating gelatin particles grow first toward the periphery of the bead where there is the greatest concentration of oxygen and nutrients. As the standard alginate bead is cultured it softens and cell clusters can be noted throughout the alginate matrix and are visible to the naked eye.

However, when the same cells are grown in the inventive alginate beads formulated with gelatin particles, they form larger clusters of cells at a faster growth rate then in standard alginate beads. The cells which are immobilized in the novel alginate-gelatin matrix grow into the cavities created by the gelatin and once inside a cavity continue to grow completely filling it. This growth increases cell density within the bead which is reflected in an increased productivity of the cells.

The improved production of cells obtained with the inventive alginate-gelatin beads in a bioreactor indicate that cell density is increased over yields obtained with conventional beads using a smaller volume bioreactor. Production yields according to the present invention have tripled over prior art methods as demonstrated by the following examples.

The following examples are illustrative only and are not meant to limit the scope of the invention in any way. The examples were performed as written.

EXAMPLE 1

A hybridoma cell line, designated Li-8, producing monoclonal antibodies to a human recombinant leukocyte interferon was made as described in Staehlin, T. et al., *PNAS* 78:3 pp. 1848-52 (1981). The stock hybridoma cells were maintained by conventional methods in Iscove's Modified Dulbecco's medium supplemented with 2.5% fetal calf serum (FCS).

An alginate solution of the present invention was prepared by mixing 1.6 grams of alginate per 100 ml of Iscove's growth medium at room temperature to form a 1.6% weight/volume alginate solution.

Sterile gelatin particles were prepared by autoclaving porcine skin gelatin, 300 bloom, obtained from Sigma at 15 psi at 121° C. for 15 minutes in a flask. Gelatin particles were then reformed by inserting a sterile stirring bar into the flask and vigorously shaking on a mechanical shaker. A gelatin suspension solution of 2.5% weight/volume was prepared by adding 20 grams of sterile gelatin granules to 400 ml of Iscove's growth medium.

The hybridoma cells were mixed with the gelatin particles by removing the cells from the Iscove's growth medium by sedimentation at 500 x g and were resuspended in Iscove's medium containing gelatin particles to from a gelatin-cell suspension. The gelatin-cell suspension was mixed with the alginate solution to form the following solution per liter; 530 ml of 1.6% weight/volume alginate solution and 470 ml of a 2.5% weight/volume gelatin suspension containing $5 \times 10^9$ cells. The resulting sodium alginate-gelatin-cell solution was dripped into a 50 mM $CaCl_2$, 0.1M NaCl solution. As the drops come in contact with the calcium solution. The alginate polymerizes in the form of beads immobilizing the cells and the gelatin particles within the alginate matrix. The beads were then washed twice with Iscove's medium and incubated in fresh medium at 37° C. in the bioreactor. The cells were grown in the bioreactor for about 60 days at 37° C.

During the growth period, growth medium was circulated through the growth chamber at a perfusion rate of 250 ml/hr. Between day 1 and day 60 samples of medium were taken daily to measure the production of hybridoma cells. The samples were assayed on an affinity column composed of recombinant human leukocyte interferon coupled to a Sepharose gel by interferon assay procedures described in Roy, S. K. et al., *J. Chromatog* 327:189 (1985), herein incorporated by reference. Daily production rates were calculated.

For comparison prior art alginate beads were formed from a solution of $5 \times 10^9$ cells; 530 ml of 1.6% weight/volume alginate solution and 470 ml of Iscove's medium with 2.5% weight/volume FCS. The solution was incubated in the bioreactor and assayed as described above. Daily production rates for the standard alginate beads were calculated.

Figure 2:
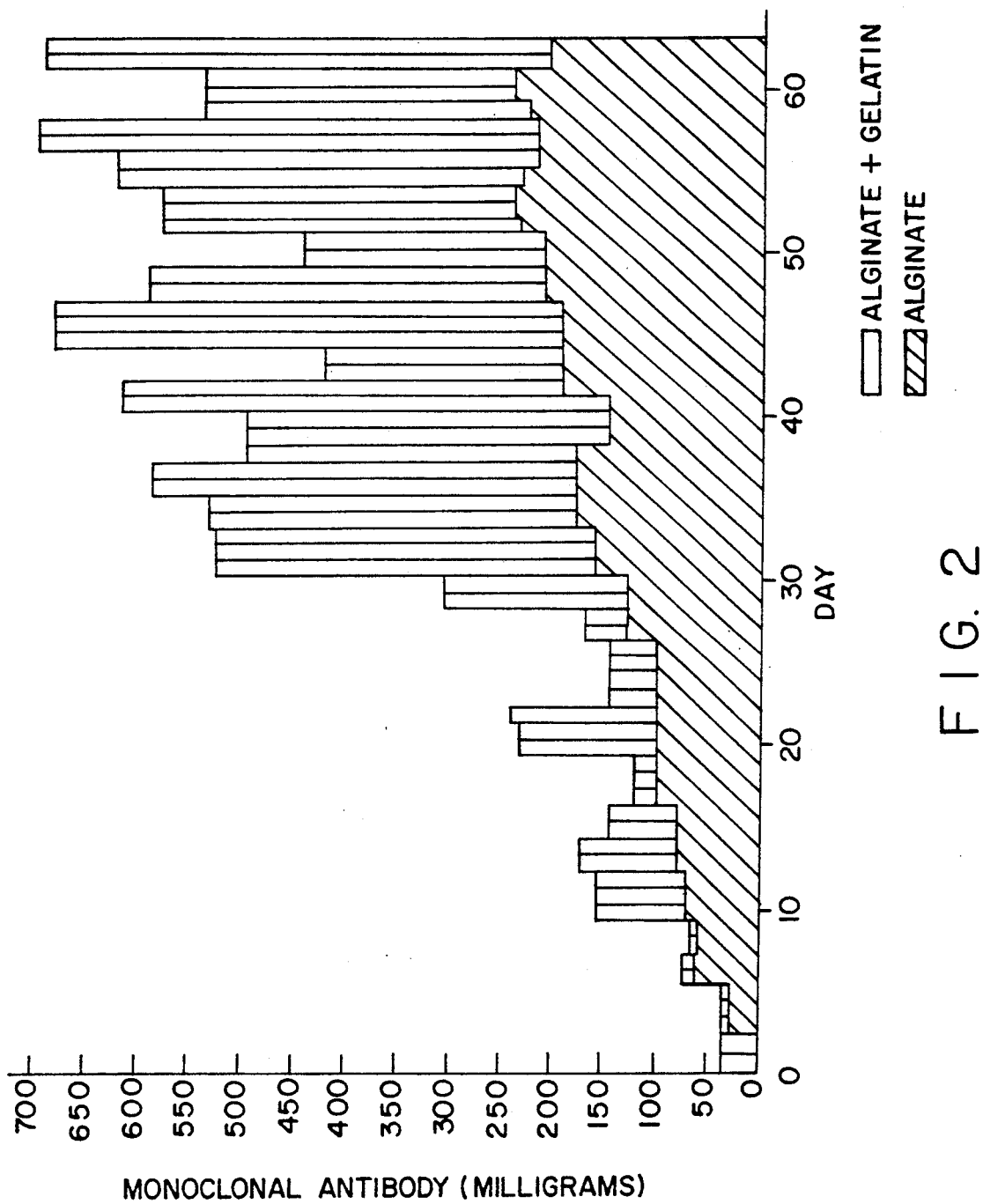
FIG. 2—is a graph comparing the increased production of hybridoma cells in a bioreactor containing alginate/gelatin beads as an immobilization material of the invention, rather than conventional alginate beads known in the art.

Daily production yields of monocolonal antibody to alpha interferon produced in the inventive alginate-gelatin-cell beads were compared to daily monoclonal antibody yields produced in prior art alginate beads and illustrated in FIG. 2. Open bars in FIG. 2 illustrate yields from the inventive beads while closed bars illustrate yields from the prior art beads.

The following results were noted in comparing the use of inventive beads and prior art beads. During the production phase (i.e., about day 30 to day 60) the total antibody production of the inventive alginate/gelatin beads was about 15 g of monoclonal antibody as compared to only 4.5 g of monoclonal antibody in the alginate beads without gelatin. During the production phase the average production of monoclonal antibody was about 500 mg per day in the alginate-gelatin beads as compared to only 150 mg/day from the standard alginate beads as illustrated in FIG. 2. Therefore, the average daily production rate was increased about three-fold with the inventive beads. Also a consistent increase of cell growth during the production phase at a faster growth rate was observed with the alginate-gelatin beads, as compared to the cell growth observed in the standard beads.

EXAMPLE 2

According to the procedures of example 1, a hybridoma cell line (designated 35f5g10) producing antibody to Il-1 receptor protein was made as described in Staehlin, supra. The cells were resuspended in Iscove's medium containing gelatin particles and mixed with an alginate solution to form the following alginate-gelatin-cell solution per 10 ml: $1 \times 10^7$ cells; 5.3 ml of 1.6% weight/volume alginate solution; and 4.7 ml of a 2.5% weight/volume gelatin suspension.

In accordance with the procedures of example 1, the total production of the harvested cells over 6 days of production yielded 1.5 g of monoclonal antibody grown in the alginate-gelatin beads as opposed to 0.6 g of monoclonal antibody grown in the prior art alginate beads. Production in the inventive beads consistently increased at a faster rate as compared to production rates observed in the standard beads.

EXAMPLE 3

Again following the procedures of Example 1, a hybridoma cell line (designated 12a6) producing antibody to Ill receptor protein was cultured and mixed with alginate and gelatin to form the following solution per 10 ml: $2.5 \times 10^7$ cells; 5.3 ml of a 1.6% weight/volume alginate solution and 4.7 ml of a 2.5% weight/volume gelatin suspension.

Total production of monoclonal antibody over a 4 day period in the alginate-gelatin beads was 2.8 g as compared to a yield of only 1.3 g in the standard beads.

A preferred airlift bioreactor system for use with the novel invention is shown in FIG. 1. The system includes a bioreactor 1 within a temperature control water jacket 30. The temperature control water jacket 30 has a water inlet 31 for receiving temperature controlled water from suitable temperature control means (not shown). The temperature controlled water exits the temperature control jacket 30 via outlet 32. The temperature control jacket preferably maintains the bioreactor 1 at a preselected temperature suitable for cell growth.

The bioreactor 1 has from top to bottom a growth chamber 10 including immobilization means 120. The growth chamber 10 is connected via a downwardly and inwardly sloping conical section 21 to a mixing chamber 20 of smaller diameter than the growth chamber 10.

A preferred airlift bioreactor for use in the present invention is described in U.S. Pat. No. 4,649,117, issued on March 10, 1987 to Familletti, the specification of which is incorporated herein by reference.

According to the invention, a cell immobilization material 120 is preferably made by forming beads of alginate-gelatin-cells as described above. A solution of alginate, preferably containing about 0.85 to about 4% weight/volume alginate in a growth medium containing NaCl is made at room temperature. A cell suspension is made. A gelatin particle solution is made of about 5% to about 25% weight/volume gelatin in growth medium, and the solutions of alginate and gelatin-cells are mixed together. The alginate-gelatin cell solution is then dripped dropwise through a multiport manifold 90 into a solution of $CaCl_2$ and NaCl in the bioreactor 1 to polymerize the alginate to form a matrix and to entrap the cells and gelatin within the matrix. It may be appreciated that the calcium solution may be in a container separate from the bioreactor 1, such as a flask or beaker and the formed beads may be added to the bioreactor after the alginate-cell-gelatin solution is polymerized.

After the beads are formed, the beads are washed with liquid growth medium 130 and the cell immobilization material 120 is maintained in the bioreactor at optimum conditions. The beads are incubated at elevated temperatures to dissolve the gelatin particles and form cavities within the alginate matrices which contain the cells to be grown. Liquid growth medium 130 is introduced into the bioreactor 1 by medium pump 80 via medium feed line 81 until the growth chamber 10 is partly filled.

Gas is then sparged up through the liquid growth medium 130 within the bioreactor 1 via gas sparger 51. The upwardly flowing gas constitutes a stream of gas bubbles which instigates a gentle circulation of liquid growth medium 130 within the bioreactor 1. This gentle circulation is denoted by arrows 131.

As can be seen in FIG. 1, cell immobilization material, preferably alginate-gelatin beads 120, is positioned within bioreactor 1 so as to intersect at least a portion of the liquid growth medium 130 which is gently circulating within the bioreactor 1. Preferably, the immobilization material is positioned within the growth chamber 10.

In operation, factors such as glucose, various nutrients, and sodium hydroxide to control the pH, etc. may be introduced as needed into growth chamber 10 via the factor feed line 100.

From time to time or on a continuous basis spent liquid growth medium may be withdrawn from the bioreactor 1 via media harvest line 71 using pump 70 and replaced with fresh liquid growth medium via media feed line 81 and pump 80. Medium replacement is preferably accomplished by stopping the sparging of gas through the medium 130 and allowing the beads 120 to settle within the growth chamber 10. The liquid growth medium 130 is then removed and replaced with fresh liquid medium, and the gas is again sparged through the medium via the gas sparge 51. Biological products produced by the suspension cells entrapped in the beads 120 may be harvested from the liquid growth medium using known methods.

In the manner as described above, attachment cells can be grown in the bioreactor which produce biological products which are then recovered from the harvested liquid growth medium using known methods.

Preferably, the gas being introduced into the bioreactor 1 is a mixture of $CO_2$ and oxygen containing gas, such as air. Flow meter 40 is used to adjust in known manner the relative mixture of $CO_2$ to air in known manner based on the oxygen demand of the cells being grown as well as the pH of the liquid growth medium 130 within bioreactor 1 while the total flow rate of both gases is controlled by pump 50.

The bioreactor may contain various sensors (not shown) for measuring the pH, temperature and oxygen content of the liquid growth medium 130. Additionally, these sensors may be connected to a preprogramable microprocessor (also not shown) for controlling in known manner the various pumps which have been illustrated herein.

As can be seen from the foregoing description and examples, the bioreactor incorporating the alginate-gelatin-cell immobilization material according to the present invention is well suited to the growth of cells, such as the hybridoma cell line illustrated.

As previously mentioned, another advantage of the use of alginate-gelatin formulations as a cell immobilization material in an airlift bioreactor according to the invention is the entrapment of air bubbles within the material which diffuses from the circulating liquid growth medium.

The foregoing description of the preferred embodiments have been provided for the purpose of illustrating the invention but is not meant to limit the scope of thereof to the particular embodiments described.

I claim:

1. A method for carrying out cell culture in a bioreactor having a growth chamber for receiving the cells, comprising:
   a) selecting cells to be grown in the bioreactor;
   b) selecting alginate which is liquid where in a non-polymerized state and semi-solid when in a polymerized state;
   c) combining a liquid growth medium and the alginate to form an alginate solution;
   d) selecting gelatin particles which are solid at about room temperature and liquid at pre-selected elevated temperature;
   e) combining the cells with the gelatin particles to form a cell-gelatin particle suspension;
   f) mixing the alginate solution with the cell-gelatin particle suspension to form an alginate-cell-gelatin suspension;
   g) introducing the alginate-cell-gelatin suspension into the growth chamber of the bioreactor and polymerizing the alginate to form alginate beads having the cells and gelatin particles entrapped therein;
   h) heating the alginate beads within the growth chamber to dissolve the gelatin particles and thereby form cavities within the alginate beads said cavities containing the cells to be grown in the bioractor;
   i) introducing growth medium into the growth chamber of the bioreactor into contact with said alginate beads and introducing a gentle stream of oxygen containing gas up through the growth medium at a flow rate which is sufficient to lift liquid growth medium while contacting said alginate beads in the growth chamber; and
   j) recirculating upwardly lifted liquid growth medium in contact with said alginate beads so that oxygen is absorbed from the liquid growth medium into the cavities of the alginate beads whereby growth of the cells occurs in the cavities.

2. The method of claim 1 wherein the alginate is about 0.85 to about 4% weight/volume of the polymer matrix and the gelatin particles are about 2.5% weight/volume to about 25% weight/volume of the polymer matrix.

3. The method of claim 1, wherein said polymerizing step comprises adding the alginate-cell-gelatin suspension to a solution of calcium chloride and sodium chloride in the growth chamber to polymerize the alginate to form beads.

4. The method of claim 1 wherein the growth medium during growth of the cells is maintained at a preselected incubation temperature.

5. The method of claim 4 wherein said preselected temperature is about 37° C.

6. The method of claim 1 wherein said cells are eukaryotic or prokaryotic.

7. The method of claim 1 wherein said cells are suspension cells.

* * * * *

UNITED STATES PATENT AND TRADEMARK OFFICE
CERTIFICATE OF CORRECTION

PATENT NO. : 5,073,491
DATED : December 17, 1991
INVENTOR(S) : Philip C. Familletti It is certified that error appears in the above-identified patent and that said Letters Patent is hereby corrected as shown below:

Column 9, Claim 1, (Step b, first line) change "where in" to

-- when in --.

Signed and Sealed this

Eighth Day of March, 1994

Attest:

BRUCE LEHMAN

*Attesting Officer*    Commissioner of Patents and Trademarks